United States Patent [19]

Kotani et al.

[11] Patent Number: 5,691,433
[45] Date of Patent: Nov. 25, 1997

[54] SILICON-CONTAINING POLYMER, PROCESS FOR PREPARING THE SAME AND MONOMER THEREOF

[75] Inventors: Jun Kotani; Manabu Tsumura; Takahisa Iwahara; Toshifumi Hirose, all of Hyogo, Japan

[73] Assignee: Kanegafuchi Chemical Industry Co., Ltd., Osaka, Japan

[21] Appl. No.: 623,515

[22] Filed: Mar. 28, 1996

Related U.S. Application Data

[63] Continuation of Ser. No. 365,131, Dec. 28, 1994, abandoned.

[30] Foreign Application Priority Data

| Dec. 28, 1993 | [JP] | Japan | 5-355128 |
| Mar. 24, 1994 | [JP] | Japan | 6-053775 |

[51] Int. Cl.$^6$ ................................................ C08G 77/60
[52] U.S. Cl. ........................ 528/15; 528/31; 528/32; 528/35; 556/432; 556/433
[58] Field of Search .......................... 528/15, 31, 32, 528/35; 556/432, 433

[56] References Cited

U.S. PATENT DOCUMENTS

| 3,050,542 | 8/1962 | Piccoli | 556/432 |
| 3,209,018 | 9/1965 | Merker | 556/432 |
| 3,318,935 | 5/1967 | Sporck | 556/433 |
| 3,576,020 | 4/1971 | Loree et al. | 556/432 |
| 4,233,427 | 11/1980 | Bargain et al. | 525/478 |
| 5,244,733 | 9/1993 | Kozakai et al. | 428/378 |
| 5,378,790 | 1/1995 | Michalczyk et al. | 528/35 |

FOREIGN PATENT DOCUMENTS 0 510 655  10/1992  European Pat. Off.

OTHER PUBLICATIONS

"Polymeric Organosilicon Systems.XVII.Synthesis and Photochemical and Conducting Properties of Poly[o– and m–(disilanylene) phenylene]s" Ishikawa et al., Journal of Polymer Science–Part A: Polymer Chemistry Edition, Dec. 31, 1993, No. 13, New York, U.S.A., pp. 3281–3289.

*Primary Examiner*—Margaret W. Glass
*Attorney, Agent, or Firm*—Foley & Lardner

[57] ABSTRACT

A silicon-containing polymer comprising a structural unit of the formula (1):

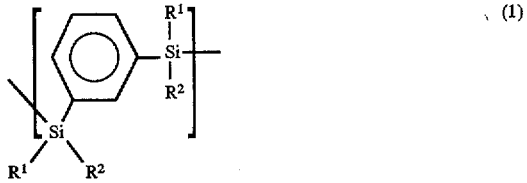

wherein $R^1$ and $R^2$ are the same or different and represent a monovalent organic group having 1 to 20 carbon atoms, and the benzene ring may have a substituent, which has good heat resistance.

5 Claims, No Drawings

SILICON-CONTAINING POLYMER, PROCESS FOR PREPARING THE SAME AND MONOMER THEREOF

This application is a continuation of application Ser. No. 08/365,131, filed Dec. 28, 1994 abandoned.

BACKGROUND OF THE INVENTION

1. Field of the Invention

The present invention relates to a heat resistant silicon-containing polymer, a process for preparing the same, and a monomer for said polymer.

2. Description of the Related Art

As a silicon-containing polymer, polysiloxane is well known. In addition to the polysiloxane having a backbone which comprises siloxane bonds, a silicon-containing polymer having a backbone which comprises Si-C bonds is also known and called as polycarbosilane.

Herein, a polymer having a backbone comprising Si and C is widely named as "polycarbosilane", while a polymer having backbone comprising alternately bonded Si and C is called as polycarbosilane in a narrow sense.

As an example of the polycarbosilane, a polymer comprising the following structural unit is known:

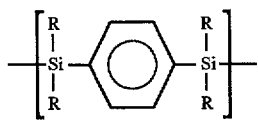

wherein R is a hydrocarbon group (cf. E. N. Znamenskaya et al., Neftekhimiya, 4, 487 (1964); N. S. Nametkin et al., Dokl. Akad. Nauk. USSR, 170, 848 (1966); and Vysokomol. Soed., 5, 921 (1966)).

The polycarbosilane as such is expected to be used as a molding material. However, this polymer has a drawback that it has a poor solubility in a solvent while it has high heat resistance since it comprises 1,4-bis(dimethysilylene) phenylene units. Further, the conventional polycarbosilane has low molding processability when it is used in the form of a coating material, a film, a fiber or a bulk or when it is used as a matrix resin of a complex.

SUMMARY OF THE INVENTION

One object of the present invention is to provide a silicon-containing polymer having good heat resistance and solubility.

Another object of the present invention is to provide a process for preparing a silicon-containing polymer.

A further object of the present invention is to provide a monomeric compound for a silicon-containing polymer.

According to the first aspect of the present invention, there is provided a silicon-containing polymer comprising a structural unit of the formula (1):

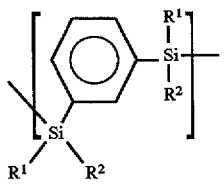

wherein $R^1$ and $R^2$ are the same or different and represent a monovalent organic group having 1 to 20 carbon atoms, and the benzene ring may have a substituent.

According to a second aspect of the present invention, there is provided a process for preparing the above silicon-containing polymer of the present invention, comprising hydrosilylaton polymerizing at least one monomer selected from the group consisting of a silicon-containing compound having two SiH groups of the formula (3):

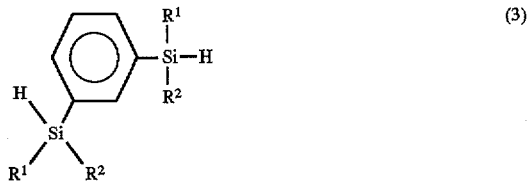

wherein $R^1$ and $R^2$ are the same as defined above and the benzene ring may have a substituent, and a silicon-containing compound having two alkenylsilyl groups of the formula (4):

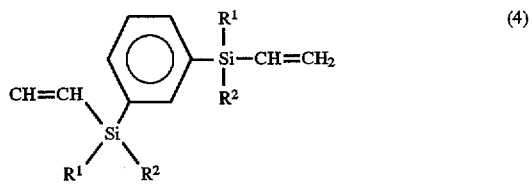

wherein $R^1$ and $R^2$ are the same as defined above and the benzene ring may have a substituent.

According to a third aspect of the present invention, there is provided 1,3-bis(diorganovinylsilyl)benzene of the formula (5):

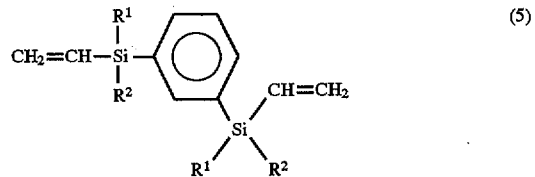

wherein $R^1$ and $R^2$ are the same.

DETAILED DESCRIPTION OF THE INVENTION

The organic group for the $R^1$ and $R^2$ groups includes straight or branched alkyl groups having 1 to 20 carbon atoms (e.g. methyl, ethyl, n-propyl, isopropyl, n-butyl, tert.-butyl, isoamyl, n-octyl, n-nonyl, etc.), aryl or aralkyl groups having 6 to 20 carbon atoms (e.g. phenyl, etc.), alklysiloxy groups (e.g. trimethylsiloxy, etc.), and the like. Among them, a methyl group and a phenyl group are preferred. A preferred combination of $R^1$ and $R^2$ is a combination of a methyl group and a methyl group, or a combination of a methyl group and a phenyl group.

The benzene ring in the structural unit (1) may have a substituent. Specific examples of the substituent are unsaturated hydrocarbon groups (e.g. a vinyl group, an allyl group, an isopropenyl group, an ethynyl group, etc.), hetero atom-containing functional groups (e.g. a hydroxyl group, an alkoxy group, an amino group, an alkylamino group, an aldehyde group, a carboxyl group, a cyano group, a nitro group, a siloxy group, etc.), a halogen atom, and the like.

In view of the heat resistance and solubility, the silicon-containing polymer of the present invention comprises, in its backbone, preferably at least 20% by weight, more preferably at least at least 50% by weight, in particular at least 60% by weight of the structural units (1), namely, the 1,3-bis(diorganosilylene)phenylene units.

In a preferred embodiment of the present invention, in addition to the structural unit (1), the silicon-containing polymer of the present invention may comprise, in its backbone, at least one other structural unit.

Examples of the other structural unit are —CH$_2$—, —CH(CH$_3$)—, —CH$_2$CH$_2$—, —CH$_2$CH$_2$CH$_2$—, —CH$_2$CH(CH$_3$)—, —C$_6$H$_4$—, and the like. Among them, —CH$_2$CH$_2$— is preferred.

When the structural unit: —CH$_2$CH$_2$— is used, the backbone of the silicon-containing polymer of the present invention comprises the structural unit of the formula (2):

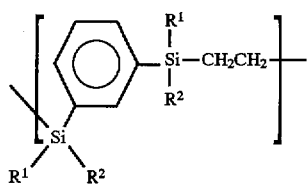
(2)

wherein R$^1$ and R$^2$ are the same as defined above and the benzene ring may have a substituent.

The silicon-containing polymer of the present invention preferably has a number average molecular weight of at least 2000, more preferably at least 5000, in particular at least 8000, when it is measured by gel permeation chromatography using a polystyrene standard. A molecular weight distribution (M$_w$/M$_n$) is preferably 5 or less, more preferably 3 or less.

The silicon-containing polymer of the present invention may be prepared by various processes. Preferred preparation process comprises hydrosilylation polymerizing at least one monomer selected from the group consisting of a silicon-containing compound having two SiH groups of the formula (3):

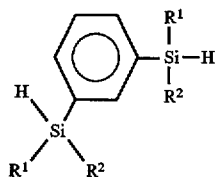
(3)

wherein R$^1$ and R$^2$ are the same as defined above and the benzene ring may have a substituent, and a silicon-containing compound having two alkenylsilyl groups of the formula (4):

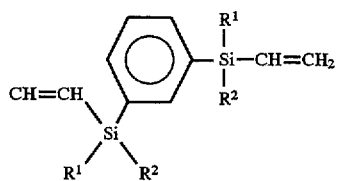
(4)

wherein R$^1$ and R$^2$ are the same as defined above and the benzene ring may have a substituent.

Preferred examples of the silicon-containing compound (3) are

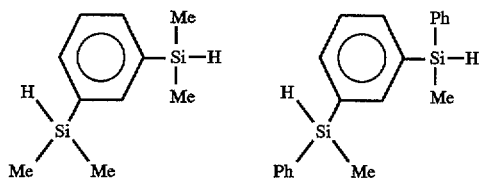

wherein Me and Ph are the same as defined.

Preferred examples of the silicon-containing compound having the alkenylsilyl group (4) are

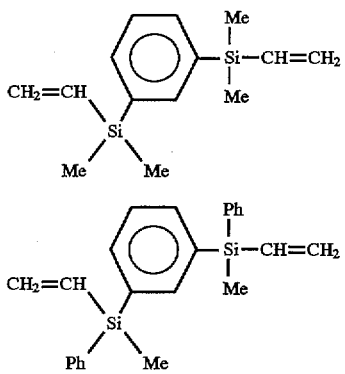

wherein Me represents a methyl group, and Ph represents a phenyl group.

When the silicon-containing compound (3) is used, it is necessary to use a compound having at least two unsaturated group in combination. Examples of the unsaturated group are a vinyl group, an isopropenyl group, an ethynyl group, and the like. Among them, the vinyl group is preferred. A specific example of the compound having at least two unsaturated group is a compound of the formula:

$$CH_2=CR'—X—CR'=CH_2 \qquad (6)$$

wherein R' is a hydrogen atom or a methyl group, and X is a single bond or a divalent organic group.

Examples of the divalent organic group for X are

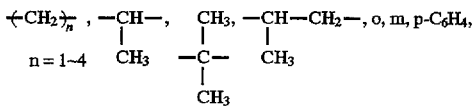

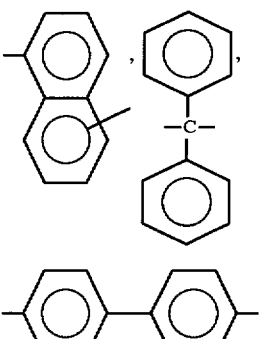

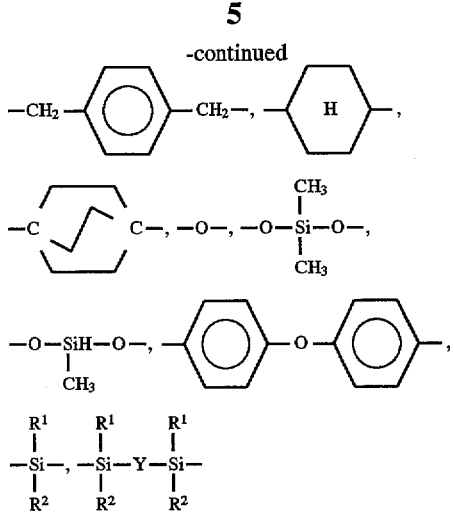

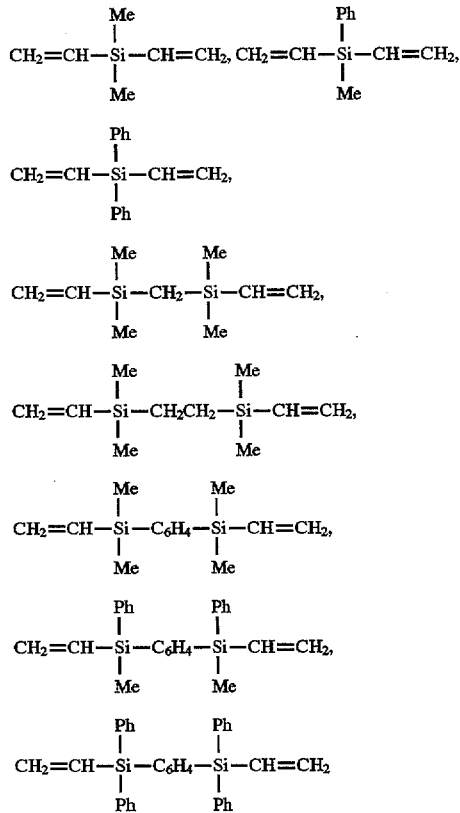

wherein Me and Ph are the same as defined above, since these compounds increase the content of silicon atoms in the polymer.

When the compound (3) is used, it is possible to use other compound having at least two hydrosilyl groups in a molecule in combination.

When the compound (4) is used, it is necessary to use a compound having at least two hydrosilyl groups in combination.

Examples of the compound having at least two hydrosilyl groups are

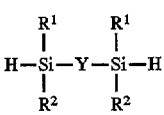

wherein $R_1$, $R_2$ and Y are the same as defined above.

Among the compounds (7) and (8), the following compounds are preferred:

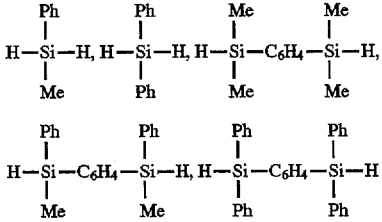

wherein Me and Ph are the same as defined above, since they increase the content of silicon atoms in the polymer.

When the compound (4) is used, it is possible to use a compound having at least two unsaturated groups in a molecule in combination.

A polymerization rate can be controlled by the use of a catalyst. A kind of the catalyst depends on the combination of the monomers. In the polymerization process of the present invention, any of conventional catalysts used for a so-called hydrosilylation reaction may be used. Examples of such catalyst are metal platinum, platinum supported on a carrier such as alumina, silica or carbon black, a complex of platinum with an alcohol, an aldehyde or a ketone, a platinum-olefin complex (e.g. $Pt(CH_2=CH_2)_2(PPh_3)_2$, $Pt(CH_2=CH_2)_2Cl_2$ (Ph=phenyl)), a platinum-vinylsiloxane complex (e.g. $Pt_n(ViMe_2SiOSiMe_2Vi)_m$, $Pt_n[(MeViSiO)_4]_m$ (Me=methyl, Vi=vinyl, m=an integer, n=an integer)), a platinum-phosphine complex (e.g. $Pt(PPh_3)_4$, $Pt(PBu)_4$ (Ph= phenyl, Bu=butyl)), a platinum-phosphite complex (e.g. $Pt[P(OPh)_3]_4$ (Ph=phenyl)), dicarbonyldichloroplatinum, a platinum-hydrocarbon complex disclosed in U.S. Pat. Nos. 3,159,601 and 3,159,662 (both to Ashby) the disclosures of which are hereby incorporated by reference, and a platinum-alcholate catalyst disclosed in U.S. Pat. No. 3,220,972 (to Lamoreaux) the disclosure of which is hereby incorporated by reference. Further, a platinum chloride-olefin complex disclosed in U.S. Pat. No. 3,516,946 (to Modic), the disclosure of which is hereby incorporated by reference, can be used in the process of the present invention.

Examples of the catalyst other than the platinum base catalysts are $RhCl(PPh_3)_3$, $PhCl_3$, $RhAl_2O_3$, $RuCl_3$, $IrCl_3$, $FeCl_3$, $AlCl_3$, $PdCl_2.2H_2O$, $NiCl_2$, $TiCl_2$, and so on.

The catalysts may be used independently or as a mixture of two or more of them.

In view of the catalytic activity, chloroplatinic acid, the platinum-olefin complex, the platinum-vinylsiloxane complex and platinum-acetyl acetonate are preferred.

An amount of the catalyst is not critical. In general, the catalyst is used in an amount of $10^{-1}$ to $10^{-8}$ mol, preferably $10^{-3}$ to $10^{-6}$ mol, per one mole of the hydrosilyl group.

The polymerization can be carried out in the presence or absence of a solvent. When the solvent is used, there is used a hydrocarbon solvent (e.g. benzene, toluene, hexane, heptane, etc.), an ether (e.g. tetrahydrofuran, 1,4-dioxane, diethyl ether, etc.), a ketone (e.g. acetone, methyl ethyl ketone, etc.), a halogen-containing solvent (e.g. chloroform, methylene chloride, 1,2-dichloromethane, etc.), and the like. Among them, toluene, tetrahydrofuran and chloroform are preferred. The solvents may be used as a mixture of two or more of them.

When the solvent is used, its amount is not larger than 50 liters per one mol of the monomer(s).

A polymerization temperature is preferably from −50° C. to 200° C., more preferably from 0° C. to 150° C.

When the polymerization temperature is lower than −50° C., a catalytic activity of the catalyst is not sufficiently high, while when it is higher than 200° C., the catalyst is deactivated by heat.

A compound of the formula (5) is a novel compound and preferably used as a monomer of the silicon-Containing polymer of the present invention:

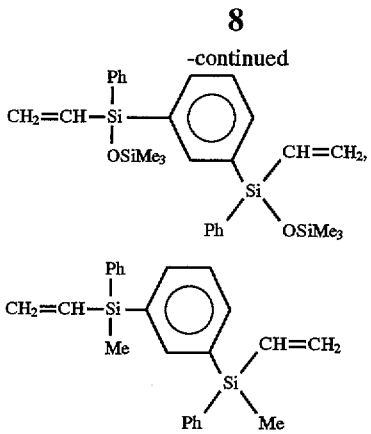
(5)

wherein $R^1$ and $R^2$ are the same as defined above.

Preferred examples of the $R^1$ and $R^2$ group are the same as those described above.

Specific examples of the compound (5) are as follows:

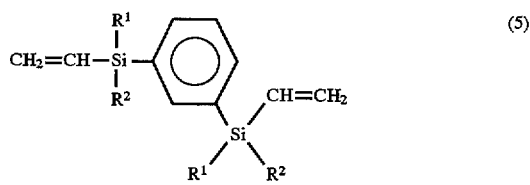

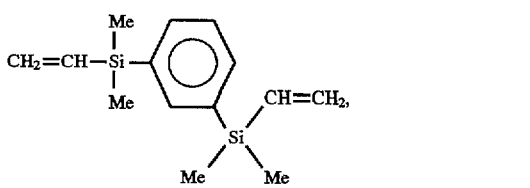

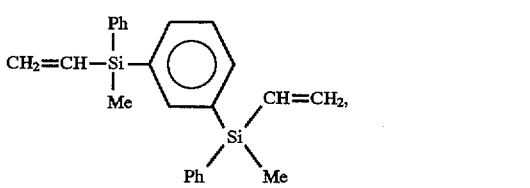

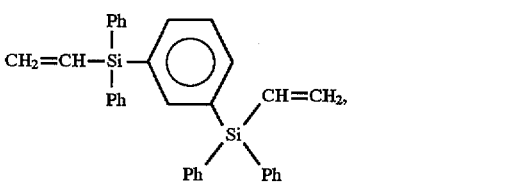

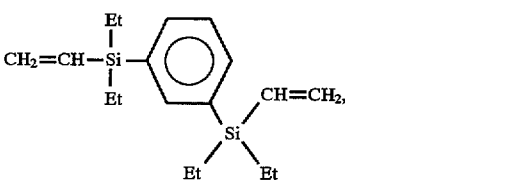

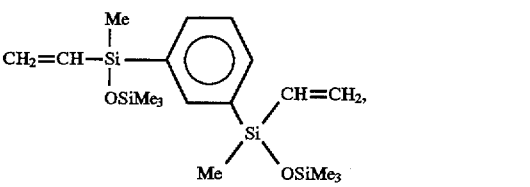

wherein Me and Ph are the same as defined above, and Et represents an ethyl group.

Among them, the following two compounds are preferred:

in view of the easiness of their synthesis, a reactivity in the synthesis of polycarbosilane, and so on.

The compound (5) may be prepared by the following process.

That is, a 1,3-dihalobenzene of the formula (9):

(9)

wherein V is a halogen atom such as a chlorine atom, a bromine atom or an iodine atom is reacted with a diorganovinylsilane compound of the formula (10):

$$CH_2=CHSiR^1R^2W \qquad (10)$$

wherein $R^1$ and $R^2$ are the same as defined above, and W is Cl, Br, I; $OR^3$ in which $R^3$ is hydrogen atom or a monovalent hydrocarbon group having at least one carbon atom such as a methyl group, an ethyl group, an isopropyl group, a butyl group, a phenyl group or a substituted phenyl group; $OCOR^4$ in which $R^4$ is the same as $R^3$; $OC(CH_3)=CH_2$, $O-N=CR^5R^6$ in which $R^5$ and $R^6$ are the same or different and represent a monovalent hydrocarbon group having at least one carbon atom; $NR^7R^8$ in which $R^7$ and $R^8$ are the same or different and a hydrocarbon group having at least one carbon atom; $N(R^9)COR^{10}$ in which $R^9$ and $R^{10}$ are the same or different and a hydrogen atom or a hydrocarbon group having at least one carbon atom, in the presence of magnesium in an ether solvent such as tetrahydrofuran or diethyl ether. This reaction proceeds according to the following reaction formula (11):

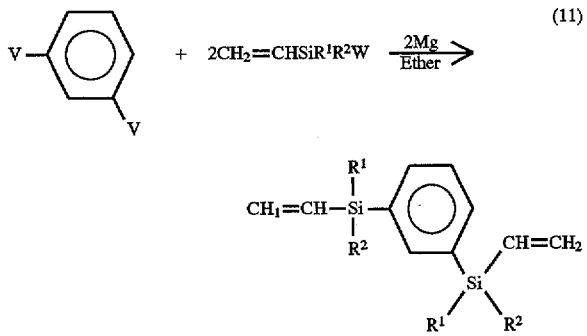

Specific examples of the 1,3-dihalobenzene (9) are

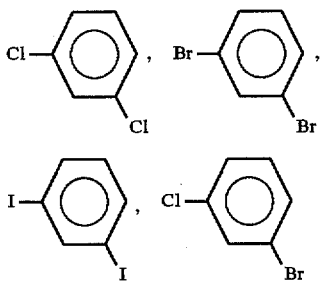

Among them, 1,3-dibromobenzene is preferred in view of the reactivity and easy availability.

Specific examples of the diorganovinylsilane compound (10) are as follows:
$CH_2=CHSiMe_2Cl$, $CH_2=CHSiPhMeCl$, $CH_2=CHSiPh_2Cl$, $CH_2=CH—SiEtMeCl$, $CH_2=CHSiEt_2Cl$, $CH_2=CHSi(n-Pr)_2Cl$, $CH_2=CH—Si(i-Pr)_2Cl$, $CH_2=CHSi(n-Bu)_2Cl$, $CH_2=CHSi(p-Tol)MeCl$, $CH_2=CHSiMe(OSiMe_3)Cl$, $CH_2=CHSi(OSiMe_3)_2Cl$, $CH_2=CHSiPh(OSiMe_3)Cl$, $CH_2=CHSiMe_2Br$, $CH_2=CHSiPhMeBr$, $CH_2=CHSiMe_2I$, $CH_2=CHSiMe_2OR^3$, $CH_2=CHSiPhMe—OR^3$, $CH_2=CHSiPhOR^2$, $CH_2=CHSiMe_2OCH(CH_3)=CH_2$, $CH_2=CHSiPhMe—OCH(CH_3)=CH_2$, $CH_2=CHSiMe_2OCOCH_3$, $CH_2=CHSiPhMeOCOCH_3$, $CH_2=CH—SiMe_2ON=CMeEt$, $CH_2=CHSiPhMeON=MeEt$, $CH_2=CHSiMe_2NMe_2$, $CH_2=CH—SiPhMeNMe_2$, $CH_2=CHSiMe_2NMeCOCH_3$, $CH_2=CHSiPhMeNMeCOCH_3$, $CH_2=CHSiMe_2OH$, $CH_2=CHSiPhMeOH$, $CH_2=CHSiPh_2OH$, $CH_2=CHSiMe—(OSiMe_3)OH$, $CH_2=CHSi(OSiMe_3)_2OH$, $CH_2=CHSi(OSiMe_3)OH$, and the like, wherein $R^2$ and $R^3$ are the same as defined above. In the above formulas, Me, Et and Ph are the same as defined above, n-Pr represents a n-propyl group, i-Pr represents an isopropyl group, n-Bu represents a n-butyl group, and p-Tol represents a p-tolyl group.

Among them, the following compounds are preferred in view of the reactivity, easy availability and storage stability:
$CH_2=CHSiMe_2Cl$, $CH_2=CHSiPhMeCl$, $CH_2=CHSiPh_2Cl$, $CH_2=CHSiEtMeCl$, $CH_2=CHSiEt_2Cl$, $CH_2=CHSiMe(OSiMe_3)Cl$, $CH_2=CH—SiPh(OSiMe_3)Cl$, $CH_2—CHSiMe_2OMe$, $CH_2=CHSiPhMeOMe$, $CH_2=CHSiMe_2—OEt$, $CH_2=CHSiPhMeOEt$, $CH_2=CHSiMe_2OCH(CH_3)=CH_2$, $CH_2=CHSiphMe—OCH(CH_3)=CH_2$, $CH_2=CHSiMe_2Cl$, $CH_2=CHSiPhMeOH$, $CH_2=CHSiPh_2OH$, $CH_2=CHSiMe(OSiMe_3)OH$, and $CH_2=CHSiPh(OSiMe_3)OH$.

Further, $CH_2=CHSiMe_2Cl$, $CH_2=CHSiPhMeCl$, and $CH_2=CHSiPh_2Cl$ are more preferred.

In the reaction represented by the reaction formula (11), the 1,3-dihalobenzene and magnesium may form a corresponding 1,3-di-Grignard reagent, and then the Grignard reagent and the silicon-containing compound may couple to form the compound (5).

Then, if an organic metal reagent having substantially the same reactivity as the 1,3-di-Grignard reagent is formed previously or in the reaction system, any other organic metal reagent may be used in place of the combination of the 1,3-dihalobenzene and magnesium. To form such organic metal reagent, it may be possible to use metal lithium, sodium, potassium, sodium/potassium alloy and so on in combination with the 1,3-dihalobenzene.

Alternatively, the compound (5) can be prepared by using a dialkoxysilane of the formula (12):

$$R^1R^2Si(OR^3)_2 \qquad (12)$$

wherein $R^1$, $R^2$ and $R^3$ are the same as defined above in place of the organic silicon-containing compound (10) in the reaction according to the reaction formula (11).

In this reaction, since the dialkoxysilane (12) has a suitable reactivity with the 1,3-di-Grignard reagent which is formed form the 1,3-dihalobenzene and magnesium, a 1,3-bis(alkoxydiorgano)benzene of the formula (13):

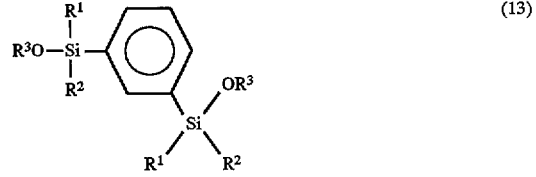

wherein $R^1$, $R^2$ and $R^3$ are the same as defined above is obtained with a high selectivity. This reaction proceeds as follows:

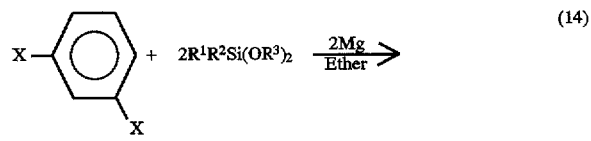

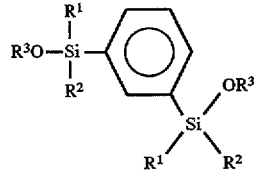

Then the alkoxy group in the 1,3-bis(alkoxydiorgano) benzene (13) can be replaced by a suitable chemical replacement to obtain the 1,3-bis(diorganovinylsilyl)benzene (5). For example, the 1,3-bis(alkoxydiorgano)benzene is reacted with a vinyl Grignard reagent or a vinyl lithium reagent in a solvent such as tetrahydrofuran or diethyl ether to obtain the 1,3-bis(diorganovinylsilyl)benzene according to the reaction formula (15):

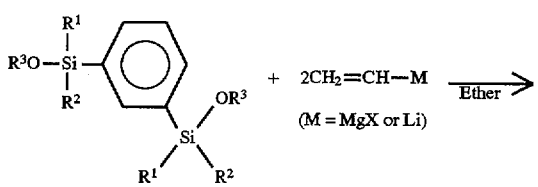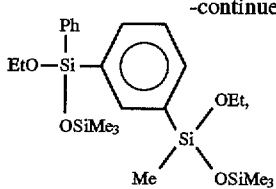 (15)

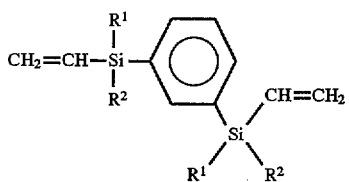

Specific examples of the dialkoxysilane (12) are Me₂Si—(OMe)₂, Me₂Si(OEt)₂, PhMeSi(OMe)₂, PhMeSi(OEt)₂, (Me₃SiO)Me—Si(OMe)₂, (Me₃SiO)PhSi(OMe)₂, (Me₃SiO)MeSi(OEt)₂, (Me₃SiO)Ph—Si(OEt)₂, Ph₂Si(OMe)₂, Ph₂Si(OEt)₂, Et₂Si(OMe)₂, Et₂Si(OMe)₂, Et₂Si(OEt)₂, EtMeSi(OMe)₂, EtMeSi(OEt)₂, PhEtSi(OMe)₂, PhEtSi(OEt)₂, Me₂Si(O-i-Pr)₂, PhMeSi(O-i-Pr)₂, PhEtSi(O-i-Pr)₂, and the like.

Among them, Me₂Si(OMe)₂, Me₂Si(OEt)₂, PhMeSi(OMe)₂, and PhMeSi(OEt)₂ are preferred in view of the selectivity of the reaction and easy availability.

Specific examples of the compound (13) obtained by the reaction (14) are

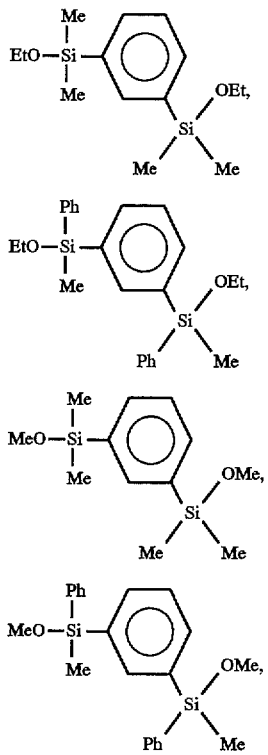

When the compound (5) is hydrosilylation polymerized, the highly heat resistant polycarbosilane of the present invention comprising the 1,3-bis(diorganosilylene) phenylene unit which is effective to the improvement of the solubility because of its flexibility is obtained.

The heat resistant silicon-containing polymer of the present invention can be used as a heat resistant coating, a heat resistant paint, or a prepreg for the production of a heat resistant part used around an engine or a heat resistant light weight construction material.

The present invention will be illustrated by the following examples, which do not limit the scope of the present invention in any way.

Synthesis Example 1

Preparation of 1,3-bis(ethoxydimethylsilyl)benzene

In a flask containing dried magnesium (4.81 g, 0.198 mol), Me₂Si(OEt)₂ (26.81 g, 0.181 mol) and tetrahydrofuran (THF) (10 ml) were charged. Then, about 1 ml of a solution of 1,3-dibromobenzene (20.31 g, 0.0861 mol) dissolved in THF (25 ml) was added under a nitrogen atmosphere, and the mixture was heated to start the reaction. Another 1 ml of the solution was added after 20 minutes. While maintaining the heat generation, the rest of the solution of 1,3-dibromobenzene was dropwise added over about 45 minutes. After the addition of the solution, the mixture was heated while refluxing THF.

After consumption of the starting material was confirmed by gas chromatography (GC), THF and formed salt were removed. By distillation under reduced pressure, a desired product was obtained as a colorless transparent liquid. Yielded amount: 3.81 g (0.048 mol). Yield: 57%. Boiling point: 84°–86° C./0.82–0.9 Torr.

$^1$H-NMR (δ, CDCl₃): 0.40 (s, SiCH₃, 12H), 1.20 (t, OCH₂CH₃, J=7.3 Hz, 6H), 3.69 (q, OCH₂CH₃, J=7.3 Hz, 4H), 7.40 (t, aromatic J=7.4 Hz, 1H), 7.62 (d, aromatic, J=7.4 Hz, 2H), 7.81 (s, aromatic, 1H).

Example 1

Preparation of 1,3-bis(vinyldimethylsilyl)benzene

In a flask, 1,3-bis(ethoxydimethylsilyl)benzene prepared in Synthesis Example 1 (13.81 g, 49 mmol) and THF (10 ml) were charged. Under a nitrogen atmosphere, a 1.0M solution of CH₂=CHMgBr in THF (108 ml, 108 mmol) was dropwise added to the mixture in the flask at room temperature over about 30 minutes. After the addition of the Grignard reagent, THF was refluxed for 5 hours. After keeping the mixture at room temperature overnight, the consumption of the starting compounds and the formation of the desired produced were confirmed by GC.

To the reaction mixture, methanol (10 ml) was added to decompose excessive CH₂=CHMgBr, and THF and the formed salt were removed. By distillation under reduced pressure, the above entitled compound was isolated as a colorless transparent liquid. Yield: about 30–50%. Boiling point: 75°–78° C./1.8 Torr.

$^1$H-NMR (δ, CDCl₃): 0.36 (s, Si(CH₃)₂, 12H), 5.87 (dd, CH₂=CH—, trans, J=20.3 and 4.0 Hz, 2H), 6.07 (dd, CH₂=CH—, cis, J=14.6 and 4.0 Hz, 2H), 6.31 (dd, CH$_2$=CH—, J=20.3 and 14.6 Hz, 2H), 7.35 (t, aromatic J=7.3 Hz, 2H), 7.54 (d, aromatic, J=7.3 Hz, 2H), 7.68 (s, aromatic, 1H).

Synthesis Example 2

Preparation of 1,3-bis(dimethylsilyl)benzene

In a flask containing dried magnesium (5.81 g, 0.239 mol), Me$_2$SiHCl (19.39 g, 0.205 mol) and THF (25 ml) were charged. Then, a solution of 1,3-dibromobenzene (23.03 g, 0.0976 mol) dissolved in THF (30 ml) was dropwise added at room temperature under a nitrogen atmosphere. As soon as the addition of the solution, heat was vigorously generated. Therefore, the solution was dropwise added over 1.5 hours while cooling the flask in a water bath to keep the mild heat generation. In the course of the addition of the solution, since a salt was formed, THF was added (20 ml×3).

After stirring the mixture at room temperature for 1.5 hours, the consumption of the starting compounds and the formation of the desired produced were confirmed by GC. The reaction mixture was suction filtrated through zeolite. To the residue (the liquid+salt), hexane was added and well stirred and the mixture was filtrated through a crimped filter paper. The filtrate was distilled to remove the solvent and obtain a crude product (14.9 g).

By the distillation under reduced pressure, the above entitled compound was isolated as a colorless transparent liquid. Yielded amount: 7.2 g. Yield: 38%. Boiling point: 100°–102° C./20 Torr.

$^1$H-NMR (δ, CDCl$_3$): 0.36 (d, SiH(CH$_3$)$_2$, J=3.9 Hz, J($^{13}$C—$^1$H)=119 Hz, 12H), 4.44 (septet, SiH(CH$_3$)$_2$, J=3.9 Hz, J($^{13}$C—$^1$H)=188 Hz, 1H), 7.37 (t, aromatic, J=7.0 Hz, 1H), 7.56 (d, aromatic, J=7.0 Hz, 2H), 7.73 (s, aromatic, 1H).

Synthesis Example 3

Preparation of 1,3-bis(methylphenylsilyl)benzene

In the same manner as in Synthesis Example 2 except that Mg (5.92 g, 0.24 mol), PhMeSiHCl (135.80 g, 0.223 mol) and 1,3-dibromobenzene (26.37 g, 0.112 mol) were used, the reaction was carried out in THF to obtain the above entitled compound as a colorless transparent liquid. Yielded amount: 17.36 g. Yield: 53%. Boiling point: 150°–170° C. (bath temperature)/0.60 Torr.

$^1$H-NMR (δ, CDCl$_3$): 0.62 (d, SiHPhCH$_3$, J=3.8 Hz, J($^{13}$C—$^1$H)=121 Hz, 12H), 4.94 (q, SiHPhCH$_3$, J=3.8 Hz, J($^{29}$C—$^1$H)=195 Hz, 2H), 7.29–7.44 (m, aromatic, 7H), 7.48–7.63 (m, aromatic, 6H), 7.80 (s, aromatic, 1H).

Example 2

In a solution of 1,3-bis(vinyldimethylsilyl)benzene prepared in Example 1 (1.27 g, 5 mmol) and a 1 wt. % solution of platinum-vinylsiloxane complex (5×10$^{-4}$ mmol) in toluene (6.0 μl), which were dissolved in absolute toluene (3 ml), a solution of 1,4-bis(dimethylsilyl)benzene (LS-7310 manufactured by Shin-etsu Chemical Co., Ltd.) (0.98 g, 5 mmol) dissolved in absolute toluene (3 ml) was slowly dropwise added at room temperature under a nitrogen atmosphere. The heat generation was observed for 3 to 10 minutes after the start of the heat generation, and the reaction mixture was turned pale yellow. The dropwise addition was finished in about 15 minutes. Thereafter, the mixture was stirred at room temperature for 5.5 hours following by being kept standing overnight. According to $^1$H-NMR of the reaction mixture, the disappearance of the SiH group was confirmed.

The reaction mixture was subjected to silica gel column chromatography using toluene as an eluent, and the fractions were distilled to remove toluene to obtain a crude polymer (about 2 g).

The crude polymer was purified by reprecipitating it using toluene (20 ml) and methanol (40 ml) to obtain a polycarbosilane having the following structure as a white sticky solid (1.40 g). Yield: 70%.

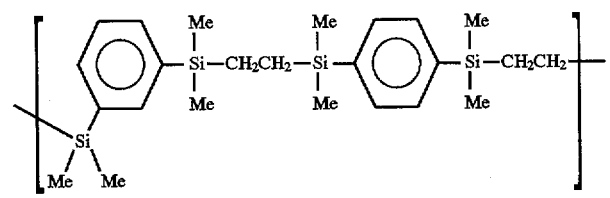

When the polymer was kept standing for several days, it was changed to a white solid. Boiling point: 64°–67° C.

A number average molecular weight was 9200 and a weight average molecular weight was 22300 by the measurement of a relative molecular weight (GPC) to the polystyrene standards using a refractometer.

$^1$H-NMR (δ, CDCl$_3$): 0.23 (s, SiCH$_3$, 12H), 0.24 (s, SiCH$_3$, 12H), 0.67 (s, SiCH$_2$CH$_2$Si, 8H), 7.27–7.66 (m, aromatic, 8H).

Example 3

In the same manner as in Example 2 except that 1,3-bis(dimethylsilyl)benzene (0.98 g, 5 mmol) was used in place of 1,4-bis(dimethylsilyl)benzene, the hydrosilylation polymerization was carried out to obtain a polycarbosilane having the following structure as a highly viscous liquid (1.49 g). Yield: 75%. The polymer had a number average molecular weight of 17000 and a weight average molecular weight of 33000 by the GPC measurement.

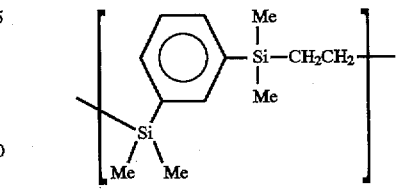

$^1$H-NMR (δ, CDCl$_3$): 0.24 (s, SiCH$_3$, 12H), 0.68 (s, SiCH$_2$CH$_2$Si, 4H), 7.24–7.65 (m, aromatic, 4H).

Example 4

In a solution of dimethylvinylsilane (LS-975 manufactured by Shin-etsu Chemical Co., Ltd.) (0.28 g, 2 mmol) and a 1 wt. % solution of platinum-vinylsiloxane complex (2.5× 10$^{-4}$ mmol) in toluene (3.0 μl), which were dissolved in absolute toluene (1 ml), a solution of 1,3-bis(methylphenylsilyl)benzene prepared in Synthesis Example 3 (0.725 g, 2.5 mmol) dissolved in absolute toluene (2 ml) was dropwise added at room temperature over 10 minutes under a nitrogen atmosphere. Then, the mixture was stirred at room temperature for 6 hours and kept standing overnight. According to $^1$H-NMR of the reaction mixture, the disappearance of the functional group of the monomer was confirmed.

The reaction mixture was distilled to remove volatile materials to obtain a white viscous liquid, which was purified and dried at 80° C. for 4 hours to obtain a polycarbosilane having the following structure as a sticky solid (0.87 g). Yield: 87%. The polymer had a number average molecular weight of 4800 and a weight average molecular weight of 10000 by the GPC measurement.

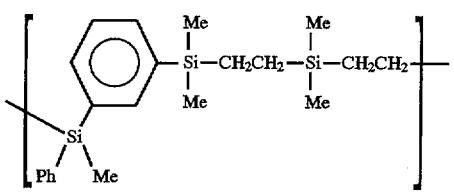

¹H-NMR (δ, CDCl₃): −0.10 (s, Si(CH₃)₂, 6H), 0.35–0.58 (m, —CH₂CH₂Si(CH₃)₂CH₂CH₂— and SiPh(CH₃), 10H including a pair of singlets of [SiPh(CH₃)] at 0.479 (3H)), 0.72–0.93 (m, —CH₂CH₂SiPh(CH₃)ₘ—C₆H₄—SiPh(CH₃)CH₂CH₂—, 4H), 7.14–7.77 (m, aromatic, 14H).

Comparative Example 1

In a solution of 1,4-bis(vinyldimethylsilyl)benzene (18.49 g, 75 mmol) and a 1 wt. % solution of platinum-vinylsiloxane complex (1×10⁻² mmol) in toluene (120 μl), which were dissolved in toluene (50 ml), a solution of 1,4-bis(dimethylsilyl)benzene (LS-7301 manufactured by Shin-etsu Chemical Co., Ltd.) (9.72 g, 50 mmol) dissolved in toluene (50 ml) was slowly dropwise added at room temperature under a nitrogen atmosphere. When 30 ml of the latter toluene solution was added, the viscosity of the reaction mixture increased and the stirring became insufficient. Then, 25 ml of toluene was added. The dropwise addition of the latter toluene solution was finished in about 2 hours. After evaporating the solvent off, the residue was dried at 80° C. for 4 hours under reduced pressure to obtain a polycarbosilane having the following structure as a white solid (26.5 g). Yield: 94%. The polymer had a number average molecular weight of 1300 and a weight average molecular weight of 2000 by the GPC measurement.

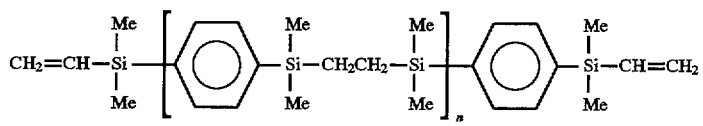

(n̄ = 4.8)

Comparative Example 2

In the same manner as in Comparative Example 1 except that 1,4-bis(vinyldimethylsilyl)benzene (615 mg, 2.5 mmol), a 1 wt. % solution of platinum-vinylsiloxane complex (5×10⁻⁴ mmol) in toluene (6 μl), 1,4-bis(dimethylsilyl)benzene (486 mg, 2.5 mmol) and toluene (5 ml) were used, the hydrosilylation polymerization was carried out to obtain a crude polycarbosilane having the following formula (300 mg). Yield: 85%. The polymer had a number average molecular weight of 15000 and a weight average molecular weight of 32000 by the GPC measurement.

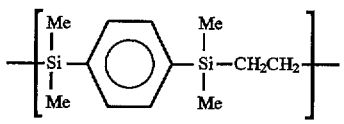

¹H-NMR (S, CDCl₃): 0.23 (s, SiCH₃, 12H), 0.68 (s, SiCH₂CH₂Si, 4H), 7.46 (m, aromatic, 4H).

With the polymers obtained in Examples 2–4 and Comparative Examples 1 and 2, heat resistance and solubility in a solvent were measured.

The heat resistance was evaluated by the thermogravimetric analysis (TGA) under a nitrogen atmosphere at a heating rate of 20° C./min. The solubility was expressed by a minimum amount of the solvent in which 1 g of each polymer was dissolved at room temperature.

The results are shown in the Table.

TABLE

| Polymer | Molecular weight | | TGA wt. loss (%) | | Solubility (ml/g) in | | |
|---|---|---|---|---|---|---|---|
| | Mn | Mw | 400° C. | 500° C. | CHCl₃ | THF | Toluene |
| Ex. 2 | 9200 | 22300 | 3 | 26 | 2 | 2 | 2 |
| Ex. 3 | 17000 | 33000 | 6 | 36 | 2 | 2 | 2 |
| Ex. 4 | 4300 | 10000 | 5 | 17 | 6 | — | — |
| C. Ex. 1 | 1300 | 2000 | 12 | 39 | 33 | 170 | 170 |
| C. Ex. 2 | 15000 | 32000 | 1 | 27 | >40 | >200 | >200 |

As seen from the results in the Table, the polymers of Examples 2, 3 and 4 had far superior solubility in the solvents to those of Comparative Examples 1 and 2 and substantially the same heat resistance as that of the comparative polymers.

What is claimed is:

1. A silicon-containing polymer comprising a structural unit of the formula (2):

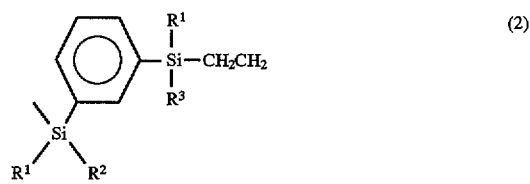

(2)

wherein $R^1$ and $R^2$ are the same or different and represent a methyl group or a phenyl group, which is obtained by hydro-silylation polymerizing at least one monomer combination selected from the group consisting of a combination of a silicon-containing compound of the formula (3):

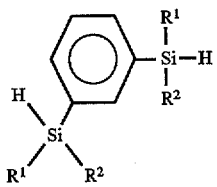 (3)

wherein $R^1$ and $R^2$ are the same as defined above and a compound having at least two unsaturated groups, and a monomer combination of a silicon-containing compound of the formula (4):

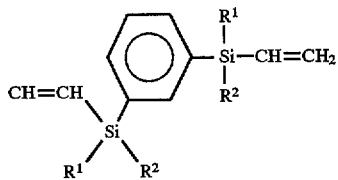 (4)

wherein $R^1$ and $R^2$ are the same as defined above and a compound having at least two hydrosilyl groups, wherein the content of said structural unit of the formula (2) is at least 50% by weight of the silicon-containing polymer.

2. The silicon-containing polymer as claimed in claim 1, wherein $R^1$ and $R^2$ are each methyl.

3. The silicon-containing polymer as claimed in claim 1, wherein said compound having at least two unsaturated groups is a compound of the formula (6):

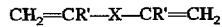 (6)

wherein $R'$ is a hydrogen atom or a methyl group, and X is a single bond or a divalent organic group.

4. The silicon-containing polymer as claimed in claim 1, wherein said compound having at least two hydrosilyl groups is at least one compound selected from the group consisting of a compound of the formula (7):

 (7)

and a compound of the formula (8):

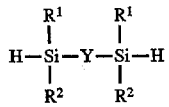 (8)

wherein $R^1$ and $R^2$ are the same or different and represent a mono-valent organic group having 1 to 20 carbon atoms, and Y is a divalent organic group.

5. A process for preparing a silicon-containing polymer comprising hydrosilylation polymerizing at least one monomer selected from the group consisting of a silicon-containing compound having two SiH groups of the formula (3):

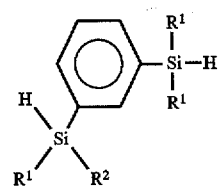 (3)

wherein $R^1$ and $R^2$ are the same or different and represent a mono-valent organic group having 1 to 20 carbon atoms and a silicon-containing compound having two alkenylsilyl groups of the formula (4):

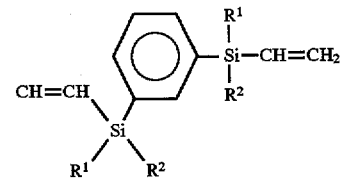 (4)

wherein $R^1$ and $R^2$ are the same as defined above and wherein said silicon-containing polymer includes at least 60% by weight of structural units of formula (1):

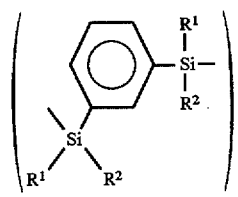 (1)

wherein $R^1$ and $R^2$ are the same or different and represent a mono-valent organic group having 1 to 20 carbon atoms.

* * * * *